(12) United States Patent
Blohm et al.

(10) Patent No.: US 10,674,891 B2
(45) Date of Patent: Jun. 9, 2020

(54) METHOD FOR ASSISTING NAVIGATION OF AN ENDOSCOPIC DEVICE

(71) Applicant: Siemens Aktiengesellschaft, München (DE)

(72) Inventors: Lutz Blohm, Möhrendorf (DE); Philip Mewes, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 921 days.

(21) Appl. No.: 14/627,937

(22) Filed: Feb. 20, 2015

(65) Prior Publication Data

US 2015/0230689 A1 Aug. 20, 2015

(30) Foreign Application Priority Data

Feb. 20, 2014 (DE) .................. 10 2014 203 097

(51) Int. Cl.

| | |
|---|---|
| *A61B 1/00* | (2006.01) |
| *A61B 5/06* | (2006.01) |
| *A61B 5/00* | (2006.01) |
| *A61B 90/00* | (2016.01) |
| *A61B 34/20* | (2016.01) |
| *A61B 34/30* | (2016.01) |

(52) U.S. Cl.
CPC ...... *A61B 1/00006* (2013.01); *A61B 1/00147* (2013.01); *A61B 5/06* (2013.01); *A61B 5/6847* (2013.01); *A61B 5/062* (2013.01); *A61B 5/4244* (2013.01); *A61B 2034/2051* (2016.02); *A61B 2034/301* (2016.02); *A61B 2090/066* (2016.02); *A61B 2090/365* (2016.02)

(58) Field of Classification Search
CPC .................. A61B 2034/107; A61B 2034/301

USPC .................................. 600/103, 424
See application file for complete search history.

(56) References Cited

U.S. PATENT DOCUMENTS

| | | | |
|---|---|---|---|
| 2009/0062646 A1 | 3/2009 | Creighton, IV et al. | |
| 2012/0035481 A1 | 2/2012 | Barbagli et al. | |
| 2012/0130171 A1* | 5/2012 | Barak ............... | A61B 1/00009 600/117 |

(Continued)

OTHER PUBLICATIONS

German Office Action for German Application No. 10 2014 203 097.8, dated Oct. 28, 2014, with English Translation.

*Primary Examiner* — Alexandra L Newton
*Assistant Examiner* — Rynae Boler
(74) *Attorney, Agent, or Firm* — Lempia Summerfield Katz LLC

(57) ABSTRACT

A method for assisting navigation of an endoscopic device using a controller with the aid of a digital image data record of an imaging examination modality is provided. The digital image data record describes an image of an object to be examined with the aid of the endoscopic device in a cavity element. A digital two-dimensional or multi-dimensional model of the object to be examined is determined based on the image data record. An operating action that predetermines a relative location of a sensor of the endoscopic device in relation to the object based on the model is received. The model is registered with the endoscopic device and/or a digital endoscopic data record supplied by the endoscopic device. An initial location of the sensor is compared with the predetermined location, and a navigation signal for navigating the endoscopic device is generated taking into account the predetermined relative location.

19 Claims, 1 Drawing Sheet

(56) References Cited

U.S. PATENT DOCUMENTS

2012/0289777 A1    11/2012  Chopra et al.
2014/0188440 A1*  7/2014  Donhowe ................ A61B 8/12
                                                                      703/1
2015/0073265 A1*  3/2015  Popovic ............... A61B 1/0005
                                                                     600/424

* cited by examiner

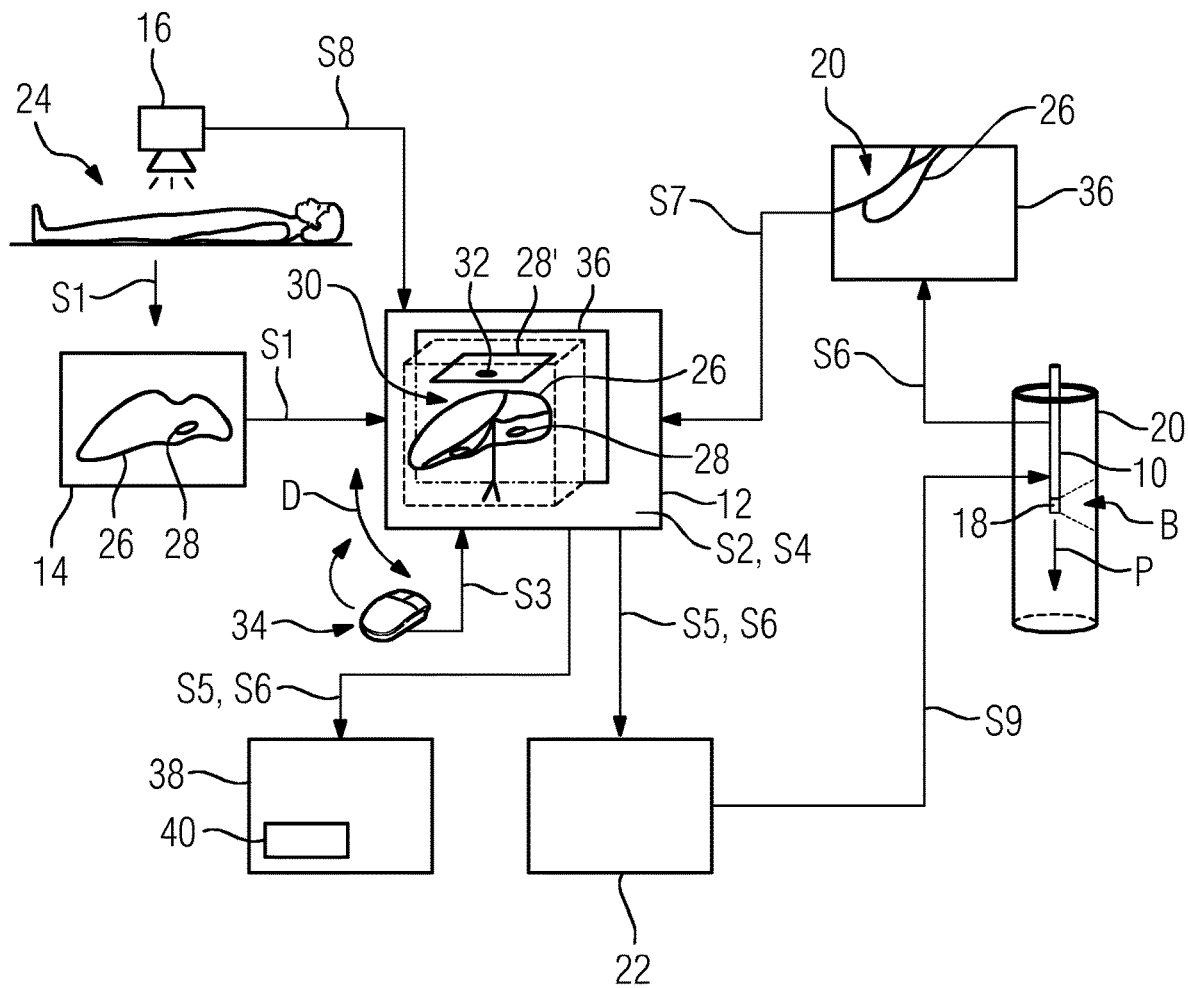

METHOD FOR ASSISTING NAVIGATION OF AN ENDOSCOPIC DEVICE

This application claims the benefit of DE 10 2014 203 097.8, filed on Feb. 20, 2014, which is hereby incorporated by reference in its entirety.

BACKGROUND

The present embodiments relate to assisting navigation of an endoscopic device with the aid of at least one digital image data record of an imaging examination modality.

The present embodiments are under the field of endoscopy and therefore deal with an examination of a cavity element with the aid of an endoscopic device. The cavity element examined may be a cavity element of a technical device or a hollow organ of a patient. In the area of minimally invasive surgery, an optical instrument (e.g., a rigid endoscope) may be introduced into different body cavities. To keep the surgical intervention as minimal as possible, such instruments are introduced into the body through a body opening or an incision, into entry openings or ports (e.g., a port in the abdominal wall of a patient or a hole in an outer wall of a cavity element of a technical device). The introduction of an endoscopic device through a port is advantageous, as the introduction reduces the trauma for a patient, for example, as much as possible. The introduction of an endoscopic device through a port may, however, also cause certain problems. One example of a problem due to such a port, which is located in an abdominal wall, for example, is the restriction of the degrees of freedom with which the endoscopic device may be moved. Cavities to be examined may therefore only be viewed to a limited degree, or it may not be possible to set an advantageous viewing angle for the object to be examined. Such a problem is referred to in the following as a compromising condition. During the course of, for example, a minimally invasive surgical intervention in the abdomen, where the port (i.e., the entry opening) is a hole in the abdominal wall, it may disadvantageously be that, for example, the liver may not be visualized from all positions and angles within the body cavity, as the movement of the endoscopic device may not be transferred at the entry opening.

Until now, this problem has been solved to some degree by using endoscopes that have an angled optical system (e.g., with an angle of 30 degrees and 70 degrees). Different viewing angles may be achieved by rotating the endoscope about an axis of the endoscope.

In the prior art, the cited disadvantage is resolved by a rigid endoscope with a flexible tip, which allows additional viewing angles and observation positions to be achieved with the aid of the flexible component enclosing the optical system. The optical system is, for example, incorporated in the tip of the endoscope. However, this approach requires extensive structural changes to the hardware and significantly restricts the resolution of the optical device (e.g., the endoscopic device, as a computer chip with a correspondingly smaller width is to be mounted on the tip). There are still problems due to the entry opening with the result that not all the viewing positions and/or viewing angles of the three-dimensional volumetric data record may be achieved with the endoscope.

SUMMARY AND DESCRIPTION

The scope of the present invention is defined solely by the appended claims and is not affected to any degree by the statements within this summary.

The present embodiments may obviate one or more of the drawbacks or limitations in the related art. For example, image quality of and information provided by an endoscopic image are improved.

One or more of the present embodiments are based on the notion of controlling the navigation of an endoscopic device, with the endoscopic view corresponding partially or completely to a view of a, for example, three-dimensional volumetric image of the imaging examination modality. In other words, navigation takes place such that a sensor of the endoscopic device is aligned based on, for example, a three-dimensional model. The exemplary three-dimensional volume (e.g., the three-dimensional image data record) is overlaid on the endoscopic image. The simultaneous view of the, for example, three-dimensional volumetric image advantageously favors a visualization of anatomical and pathological structures to assist a user with the navigation of the endoscopic device. It also allows the sensor to be located such that a predetermined point of the object to be examined may advantageously be acquired, so the sensor may produce high quality images without requiring specific technical embodiments.

The method for assisting navigation of an endoscopic device (e.g., an endoscope for a medical application or an endoscope for a technical examination) is performed by a control facility (e.g., a control device) that may be integrated in the endoscopic device or device that is separate therefrom. An endoscopic device refers, for example, to a device that may be used to examine or even change a cavity element of a living organism, as well as of a technical device.

The method is performed with the aid of at least one digital image data record of an imaging examination modality (e.g., a two-dimensional or three-dimensional image data record of an imaging examination modality in the form of an x-ray device or CT device). The at least one digital image data record in each instance describes an image of an object to be examined with the aid of the endoscopic device in the cavity element (e.g., in a hollow organ of a patient). The method includes determining a digital two-dimensional or multi-dimensional model of the object to be examined based on the at least one image data record, and receiving an operating action (e.g., a body gesture of a user) that predetermines a relative location of a sensor of the endoscopic device in relation to the object based on the model. The method also includes registering the model with the endoscopic device and/or a digital endoscopic data record supplied by the endoscopic device (e.g., with a video image of a sensor of the endoscopic device), for example, by overlaying and/or aligning the digital data records. The method also includes comparing an initial location of the sensor with the predetermined location, and generating a navigation signal for navigating the endoscopic device taking into account the predetermined relative location.

The model is a patient-specific model, in which the patient-specific anatomical structures may be identified. The model may be, for example, a two-dimensional model or a multi-dimensional image (e.g., one with more dimensions; a three-dimensional or four-dimensional image). The model may include, for example, a two-dimensional x-ray image and/or an ultrasound sectional image. This further optimizes a direction of movement of the endoscope, for example, along a navigation path, as the patient-specific anatomy is taken into account. By predetermining the relative location of the sensor, a desired viewing angle and/or a desired viewing direction may be set for a specified point of the object to be examined. A relative location of the sensor is, for example, defined as a point or position of the sensor, where the sensor is located in relation to the environment and/or an alignment of the (e.g., a positional angle or tilt of the sensor).

This allows the sensor of the endoscopic device to be brought closer to the predetermined point of an object to be examined and to be moved into a favorable position, in order to improve the information provided by and the image quality of an endoscopic image. Registering the model with the digital endoscopic data record generates augmented reality, which provides a user with an orientation aid. During an endoscopic examination, an optimal alignment and/or an optimal view is thus set for the object point. The navigation signal allows the endoscope to be steered and/or controlled. The method is independent of a position of a computer chip, allowing a larger chip to be incorporated and a higher endoscopic image resolution to be achieved.

The method is suitable for assisting navigation of the endoscopic device within a cavity element of a patient. This embodiment avoids unnecessary movement of the endoscopic device completely or to some degree, thereby preventing unnecessary trauma to the tissue of a patient or unnecessary damage to the material of the cavity element almost completely. In order not to damage any main vessels, for example, while navigating and guiding the endoscope or in order to resect tissue (e.g., a tumor), augmented reality may be deployed in minimally invasive surgery.

According to a further embodiment of the method, a navigation path from an initial location of the sensor to the predetermined relative location may be determined. This allows the predetermined location to be reached in the best possible manner. Additionally or alternatively, the predetermined location is modified to an alternative location of the sensor in a particularly advantageous manner. The determined navigation path may additionally or alternatively be modified as a function of the technical embodiment of the sensor and/or a restricting condition, which compromises the capacity for movement of the endoscopic device. In other words, a technical embodiment of the sensor, for example, includes an angle of inclination, an acquisition angle, by way of which the sensor may acquire an image of an environment, or an angle of a sensor surface. A restricting condition, which compromises the capacity for movement of the endoscopic device, is, for example, a limiting of the ability of the endoscopic device to move through an entry opening into the cavity element (e.g., a restriction due to a material, tissue or organ in proximity to the entry opening).

The entry opening may be, for example, located at a point, where a large amount of sensitive tissue or a large number of vessels are located, or may be configured as very rigid by an environment (e.g., a thick muscle layer). Taking into account the restricting condition and/or the technical embodiment of the sensor for determining the alternative location and/or the alternative navigation path allows improved accessibility to a point of the object to be examined, and there are more degrees of freedom available for the movement of the endoscopic device. This also largely prevents frequent trial and error on the part of a user when moving the endoscopic device, which also favors the complete or partial avoidance of injuries to the cavity element.

An additional increase in the number of degrees of freedom of the capacity for movement of the endoscopic device and substantial avoidance of damage or trauma to the cavity element are achieved by a further embodiment of the method. According to this, an entry position of the endoscopic device into the cavity element is determined, and the navigation path from the determined entry position to the predetermined relative location is determined. Alternatively or additionally, the determined entry position is modified as a function of a technical embodiment of the sensor and/or of a restricting condition, which compromises the capacity for movement of the endoscopic device.

According to a further embodiment of the method, the generated navigation signal may bring about the outputting of a navigation instruction by an output facility. For example, a written instruction may be output on an output facility in the form of a screen or, for example, text may be output as an instruction by an output facility in the form of a loudspeaker. A user of the endoscopic device does not therefore have to keep in mind a coordinate system of the cavity element as well as operating the endoscopic device but may concentrate on controlling the endoscopic device manually.

In order to reach the predetermined relative location or the alternative location of the sensor of the endoscopic device, according to a further embodiment of the method, a position of the sensor of the endoscopic device may be determined based on: a) an image data record supplied by an imaging examination modality; and/or b) a magnetic sensor, and/or an optical locator, an optical tracker, and/or a mechanical/kinematic, kinematic or robotic locator, or by a position signal supplied by the endoscopic device. The determined position may additionally or alternatively be transferred and/or output to the model. The use of a magnetic sensor and/or an optical locator and/or a mechanical/kinematic, kinematic or robotic locator, or a position signal supplied by the endoscopic device proves advantageous, as this does not require an additional x-ray dose for a patient.

A situation may arise, in which it is desirable to standardize the control of the endoscopic device (e.g., if tests by different laboratories are to be standardized). The method may include automatic or semi-automatic control of the endoscopic device along the navigation path by automatic or semi-automatic control of a control device connected to the endoscopic device (e.g., a robot) using the navigation signal.

In a further embodiment of the method, registration of the model with the endoscopic device and/or the digital endoscopic data record supplied by the endoscopic device may take place after receipt of the operating action. This allows the user to look first at different perspectives (e.g., different relative locations) and to select a preferred relative location. Where applicable, a specified selection of model may be stored with a specified relative location, for example, on a storage medium.

A control facility (e.g., including a processor) configured to perform a method according to one of the embodiments cited above is also provided.

An endoscopic device that includes a control device, as described above, is also provided.

A computer program product for assisting navigation of an endoscopic device including at least one non-transitory computer-readable storage medium with a program code stored thereon, which is configured, when executed by a control facility, to prompt the control facility to perform a method according to an embodiment of the method cited above, is also provided.

BRIEF DESCRIPTION OF THE DRAWINGS

Elements with same function have the same reference characters in the FIGURE.

FIG. 1 shows a schematic view of an embodiment of a method.

DETAILED DESCRIPTION

FIG. 1 shows the principle of one embodiment of a method for assisting navigation of an endoscopic device 10 using a control facility 12 (e.g., a controller) with the aid of at least one digital image data record 14 of an imaging examination modality 16. The endoscopic device 10 may include, for example, a rigid endoscope with, for example, a lens system or a flexible endoscope (e.g., a video endoscope). The endoscopic device 10 includes a sensor 18 (e.g., a lens system, a single lens or a camera). In FIG. 1, the endoscopic device 10, the sensor 18 of which covers a predetermined viewing angle due to structure of the sensor 18 and therefore acquires a field of view B, is arranged in a schematically represented cavity element 20. To perform the method, however, the endoscopic device 10 may also be arranged initially outside the cavity element 20.

The controller 12 may include a control device and in the present example is integrated in a device that is structurally separate from the endoscopic device 10. The controller 12 may, however, also be embodied as a microcontroller or chip of the endoscopic device 10 or of a further control device 22 (e.g., a robot).

An imaging examination modality 16 includes a device configured to generate a two-dimensional, three-dimensional or multi-dimensional image data record of an object 26 to be examined. For example, the imaging examination modality 16 is an x-ray device, a magnetic resonance tomography system or a computed tomography system. The digital image data record 14 generated by the imaging examination modality 16 may therefore include, for example, a two-dimensional or three-dimensional x-ray image, a magnetic resonance (MRT) scan or an image data record 14 of an exemplary computed tomography system.

In the present example, the method is used, for example, to navigate an endoscopic device 10 in the form of a medical endoscope. FIG. 1 shows a patient 24, from which the imaging examination modality 16 (e.g., a computed tomography system) supplies, for example, a three-dimensional image data record 14 or a number of digital image data records 14 of the internal organs of the patient 24 (method act S1). FIG. 1 shows the digital image data record 14 schematically as an image of an object 26 of the patient 24 to be examined (e.g., a liver). This exemplary pre-operative CT scan shows a predetermined point 28 of the object on the object 26 to be examined (e.g., a liver tumor), which is to be resected, for example, in a planned intervention. The resection act is not part of the method here. In addition to the imaging examination modality 16, further imaging examination modalities 16 may also supply one or more image data records 14 (S1). The controller 12 uses the digital image data record to determine a digital two-dimensional or multi-dimensional model 30 (S2). In the present example, in FIG. 1, the controller 12 determines, for example, a three-dimensional model 30 (S2). Widely used methods (e.g., for triangulation) are available from the prior art for the person skilled in the art when determining the three-dimensional model 30.

As indicated schematically in FIG. 1, the entire object 26 to be examined (e.g., the two hepatic lobes of the liver, a gall bladder and a portal vein) and the predetermined point 28 of the object 26 are shown. The exemplary three-dimensional model 30 also shows a representation of an abdominal wall as a further predetermined point 28'.

Changes may also be made in the exemplary three-dimensional model 30 (e.g., additional segmentation or omission of a selected structure), so that the two-dimensional or multi-dimensional model 30 does not, for example, show any arterial structures in the object 26 to be examined.

The two-dimensional or multi-dimensional model 30 advantageously shows important information relating to the object 26 to be examined, as a user may set different viewing angles and viewing positions in the two-dimensional or multi-dimensional model 30. This allows the user to identify, for example, relevant anatomical and pathological points. In the example in FIG. 1, therefore, the exemplary liver tumor may be optimally identified in the right part of the object 26 to be examined.

According to the method according to one or more of the present embodiments, the controller 12 receives an operating action (e.g., a rotation D, a movement of the two-dimensional or multi-dimensional model 30 or a selection of a specified region of the two-dimensional or multi-dimensional model 30) with a user interface 34 (e.g., a mouse) as the operating facility. The operating action D may also include, for example, a body gesture of a user. The operating action D may be acquired and determined, for example, using a camera and gesture recognition software. Additionally or alternatively, the operating action may also be used, for example, to displace a view and to set an angle or viewing direction. A relative location of the endoscopic device 10 in relation to the point 28 is then predetermined based on the operating action. From this relative location, the sensor 18 may acquire the point 28, for example, from a better angle and/or a more advantageous direction. It may also allow a user to store a selected view of the two-dimensional or multi-dimensional model 30 on a storage medium (e.g., in a cloud or on a physical data medium) in order to be able to retrieve the selected view again at a later time point.

Before the endoscopic device 10 moves to the predetermined location, the endoscopic device 10 is in a location, from which the sensor 18 may acquire the predetermined point 28, for example, but less favorably. The endoscopic device 10 supplies a digital endoscopic data record 36 (S6) (e.g., in the form of an image of the object 26 to be examined such as a liver) shown, for example, from an initial location of the endoscopic device 10. The controller 12 receives the digital endoscopic data record 36 (S7), for example, via a wired communication connection or via a wireless communication connection (e.g., WLAN).

The controller 12 registers the two-dimensional or multi-dimensional model 30 in the present example with the digital endoscopic data record 36 (S4), but this may also be done with the endoscopic device 10. Registration may take place, for example, using a feature-based or area-based method. Feature extraction, feature adjustment, transformation calculation and transformation methods are also available to the person skilled in the art for this purpose. For example, a cluster analysis or grid analysis may be performed in the process. This provides the user with an orientation aid before and during the endoscopy. The connection to augmented reality further assists the provision of further information relating to the cavity element 20.

The controller 12 may also perform a comparison between an initial location of the sensor 18 of the endoscopic device 10 and the predetermined location. The controller 12 may, for example, perform a determination of a position of the sensor 18 of the endoscopic device 10 based on an image data record supplied by the imaging examination modality 16 (or another imaging examination modality 16), for example. The supplied image data record may be supplied, for example, by an x-ray recording of the endoscopic device 10. Determination of the position of the endoscopic device 10 may take place manually or automatically. This provides a user with information about where the endoscopic device 10 and/or sensor 18 of the endoscopic device 10 is/are located. In this process, for example, a virtual image of the endoscopic device 10 in the corresponding position may be generated and displayed in the two-dimensional or multi-dimensional model 30. Such tracking may take place, for example, with the aid of an MRT scan, as this provides better resolution.

Alternatively, the position of the sensor 18 may be determined with the aid of a magnetic sensor, and/or by an optical locator (e.g., an optical tracker), and/or by a mechanical/kinematic, kinematic or robotic locator, or a position signal supplied by the endoscopic device 10. The acquired position signal may be transmitted to the controller 12 (S8). The determined position may additionally or alternatively be transferred and/or output to the model 30 (e.g., displayed in the model). A position signal acquired with the aid of a magnetic sensor (e.g., with the aid of a coil and a sensor) may be used, as unlike when the position is acquired with the aid of an imaging examination modality 16, the patient 24 is not subjected to a dose of x-ray radiation. In one embodiment, a mechanical/kinematic locator including a robot with active restriction of a capacity for movement is provided.

The controller 12 generates a navigation signal for navigating the endoscopic device 10 taking into account the predetermined relative location (S5). The generated navigation signal may be transmitted, for example, to an output facility 38 (e.g., a display unit of a computer (S6)) and may in the process, for example, bring about the outputting of a navigation instruction in a text field 40. Such a navigation instruction may, for example, include information instructing the user, for example, to move the endoscopic device 10 20 centimeters in a specified direction and/or to rotate the endoscopic device through, for example, 20 degrees to reach the predetermined location.

In order to generate the navigation signal, a navigation path from the initial location of the sensor 18 to the predetermined relative location may be determined. However, because of a technical embodiment of the sensor 18 (e.g., a symmetry and/or geometry of the endoscope tip such as an angled embodiment of the sensor surface, a predetermined viewing angle or acquisition angle of the sensor 18 and/or flexibility of a tip of the endoscopic device 10), not all the viewing positions and viewing angles, as may be seen and set in the two-dimensional or multi-dimensional model 30, may be achieved with the endoscopic device 10. According to the method, modification of the predetermined location to an alternative location and/or modification of the determined navigation path may take place as a function of a technical embodiment if, for example, a restricting condition is present, which compromises a capacity for movement of the endoscopic device 10. Such a restricting condition is, for example, a limiting of the ability of the endoscopic device 10 to move through the entry opening 32 due to the position of which the endoscopic device 10 is to be guided, for example, through a solid material (e.g., a layer of musculature). Alternatively, the endoscopic device 10 is to be inserted into the cavity in an environment where movement is limited, for example, due to the proximity of organs.

Such a restricting condition may, for example, restrict a rotation of the endoscopic device 10 in all degrees of freedom. Use of the endoscopic device 10 may provide, for example, that an environment containing critical vascular structures restricts such rotation. A parameter for the technical embodiment of the sensor 18 and/or coordinates and/or parameters for the restricting condition may be input into the controller 12, for example, manually by a user and stored there. Alternatively, the parameters may also be retrieved from an external data server and received by the controller 12.

Alternatively or additionally, the generated navigation system may be transferred to a further control device 22 (S6). Such a control device 22 (e.g., a robot) may automatically assume the perspective for the object 26 to be examined. The further control device 22 may be a robot that has torque sensors in all or some axes to detect the application of a force. Such a robot 22 may operate according to the active constraint principle and thus includes a robot with active restriction of a capacity for movement. A user may guide, for example, an arm of the robot 22 but only in one movement direction, in which movement is permitted by the navigation signal. The control device 22 may be configured to perform gravity compensation. For this, a tunnel, into which the endoscopic device 10 may be guided, is defined. The navigation signal allows automatic or semi-automatic control of the endoscopic device 10 along the determined navigation path using the endoscopic device 10. As described above, such a mechanical/kinematic locator may also be used as a locator for determining the position of the sensor 18.

In a further optional method act, an entry position 32 of the endoscopic device 10 into the cavity element 20 is determined, and the navigation path from the determined entry position 32 to the predetermined relative location is determined. A collision calculation may therefore be made according to an individual anatomy of a patient, with structures at which the endoscopic device 10 is restricted being determined. The determined entry position 32 may be modified as a function of the technical embodiment of the sensor 18 and/or of a restricting condition, which compromises a capacity for movement of the endoscopic device 10. Widely used algorithms are available to the person skilled in the art for determining an entry position 32.

The exemplary embodiment described above explains the principle of the method for controlling a position of an endoscopic device 10 so that, for example, a video image of the endoscopic device 10, a viewing direction and/or viewing angle is/are matched, for example, to a three-dimensional volumetric image (e.g., a three-dimensional model 30) of an imaging examination modality 16 (e.g., a radiological examination modality). The view of the exemplary three-dimensional volumetric image (e.g., the exemplary three-dimensional model 30) is advantageous, as a visualization of anatomical and pathological structures assists a user (e.g., a surgeon) when operating the endoscopic device 10, if the exemplary 3D volume is overlaid on an endoscopic image of an endoscopic image data record 36.

The present embodiments describe a system that automatically controls a position of an endoscopic device 10 (e.g., a medical endoscope), so that a viewing position and/or viewing angle corresponds to the viewing angle and a viewing position selected beforehand on an exemplary 3D volume (e.g., a three-dimensional model 30). This allows the use of computer-based augmented reality. The user (e.g., a physician) is able to select an optimal view of anatomies and pathologies, for example, which are based on an exemplary 3D volumetric image. A transfer of this view and/or this viewing angle to the augmented reality (e.g., into an exemplary digital endoscopic data record 36 in the form of an endoscopic image) may take place after selection.

Two solutions are proposed for reaching the desired position of the endoscopic device.

In one embodiment, the endoscopic device 10 is tracked (e.g., by acquiring and determining a position signal of the endoscopic device 10 using an electromagnetic and/or optical sensor) and may then be operated, for example, manually by the user. The sensor for acquiring the position signal may be registered in the imaging examination modality 16. The sensor and/or the controller 12 may then be guided by the user to the predetermined location or to an alternative predetermined location.

Alternatively, the endoscopic device 10 may also be positioned, for example, on a robot arm of a further control device 22. The control device 22 may, for example, being able to decode a position that was registered additionally or alternatively for the imaging examination modality 16. The further control device 22 may then guide the endoscopic device 10 to the predetermined location or the alternative location. This may take place automatically or semi-automatically.

Both cited applications may include, for example, software of the controller 12 and a restriction of the entry opening 32. Additionally or alternatively, the technical embodiment of the endoscopic device may include, for example, an angled optical system with a specified degree of angling. If such parameters are taken into account but because of the predetermined location, the predetermined location may not be reached, for example, because of a restricting condition at the entry opening 32, the system may calculate the most optimal position for the sensor 18 of the endoscopic device 10, which is very close to the predetermined location.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for assisting navigation of an endoscopic device using a controller with the aid of at least one digital image data record of an imaging examination modality, the at least one digital image data record describing an image of an object to be examined with the aid of the endoscopic device in a cavity element, the method comprising:
determining a digital two-dimensional or multi-dimensional model of the object to be examined based on the at least one image data record;
receiving an operating action that predetermines a relative location of a sensor of the endoscopic device in relation to the object based on the digital model;
registering the digital model with the endoscopic device, a digital endoscopic data record supplied by the endoscopic device, or the endoscopic device and the digital endoscopic data record;
comparing an initial location of the sensor with the predetermined relative location;
determining a navigation path from the initial location of the sensor to the predetermined relative location;
modifying the determined navigation path as a function of a technical embodiment of the sensor and a restricting condition that compromises a capacity for movement of the endoscopic device; and
generating a navigation signal for navigating the endoscopic device taking into account the predetermined relative location.

2. The method of claim 1, wherein navigation of the endoscopic device within the cavity element of a patient is assisted.

3. The method of claim 1, further comprising:
modifying the predetermined location to an alternative location.

4. The method of claim 3, further comprising:
determining an entry position of the endoscopic device into the cavity element and determining the navigation path from the determined entry position to the predetermined relative location;
modifying the determined entry position as a function of the technical embodiment of the sensor, as a function of the restricting condition that compromises the capacity for movement of the endoscopic device, or as a function of the technical embodiment of the sensor and the restricting condition;
or a combination thereof.

5. The method of claim 1, further comprising generating and outputting, by an output facility, a navigation instruction using the navigation signal.

6. The method of claim 1, further comprising:
determining a position of the sensor of the endoscopic device based on an image data record of the at least one digital image data record supplied by the imaging examination modality, based on a position signal supplied by a magnetic sensor, an optical locator, a mechanical/kinematic, kinematic, or robotic locator, or a combination thereof, or supplied by the endoscopic device, or a combination thereof;
transferring, outputting, or transferring and outputting the determined position to the digital model;
or a combination thereof.

7. The method of claim 3, further comprising automatically or semi-automatically controlling the endoscopic device along the navigation path, the controlling comprising automatically or semi-automatically controlling a control device connected to the endoscopic device using the navigation signal.

8. The method of claim 1, wherein the registering takes place after receipt of the operating action.

9. A controller comprising:
a processor configured to assist navigation of an endoscopic device with the aid of at least one digital image data record of an imaging examination modality, the at least one digital image data record describing an image of an object to be examined with the aid of the endoscopic device in a cavity element, the processor further configured to:
determine a digital two-dimensional or multi-dimensional model of the object to be examined based on the at least one image data record;
receive an operating action that predetermines a relative location of a sensor of the endoscopic device in relation to the object based on the digital model;
register the digital model with the endoscopic device, a digital endoscopic data record supplied by the endoscopic device, or the endoscopic device and the digital endoscopic data record;

compare an initial location of the sensor with the predetermined relative location;

determine a navigation path from the initial location of the sensor to the predetermined relative location;

modify the determined navigation path as a function of a technical embodiment of the sensor and a restricting condition that compromises a capacity for movement of the endoscopic device; and generate a navigation signal for navigating the endoscopic device taking into account the predetermined relative location.

10. An endoscopic device comprising:

a controller configured to assist navigation of an endoscopic device with the aid of at least one digital image data record of an imaging examination modality, the at least one digital image data record describing an image of an object to be examined with the aid of the endoscopic device in a cavity element, the controller further configured to:

determine a digital two-dimensional or multi-dimensional model of the object to be examined based on the at least one image data record;

receive an operating action that predetermines a relative location of a sensor of the endoscopic device in relation to the object based on the digital model;

register the digital model with the endoscopic device, a digital endoscopic data record supplied by the endoscopic device, or the endoscopic device and the digital endoscopic data record;

compare an initial location of the sensor with the predetermined relative location;

determine a navigation path from the initial location of the sensor to the predetermined relative location;

modify the determined navigation path as a function of a technical embodiment of the sensor and a restricting condition that compromises a capacity for movement of the endoscopic device; and generate a navigation signal for navigating the endoscopic device taking into account the predetermined relative location.

11. A computer program product comprising at least one non-transitory computer readable storage medium that stores program code having instructions executable by a controller for assisting navigation of an endoscopic device with the aid of at least one digital image data record of an imaging examination modality, the at least one digital image data record describing an image of an object to be examined with the aid of the endoscopic device in a cavity element, the instructions comprising:

determining a digital two-dimensional or multi-dimensional model of the object to be examined based on the at least one image data record;

receiving an operating action that predetermines a relative location of a sensor of the endoscopic device in relation to the object based on the digital model;

registering the digital model with the endoscopic device, a digital endoscopic data record supplied by the endoscopic device, or the endoscopic device and the digital endoscopic data record;

comparing an initial location of the sensor with the predetermined relative location;

determining a navigation path from the initial location of the sensor to the predetermined relative location;

modifying the determined navigation path as a function of a technical embodiment of the sensor a restricting condition that compromises a capacity for movement of the endoscopic device; and generating a navigation signal for navigating the endoscopic device taking into account the predetermined relative location.

12. The computer program product of claim 11, wherein navigation of the endoscopic device within the cavity element of a patient is assisted.

13. The computer program product of claim 11, wherein the instructions further comprise:

modifying the predetermined location to an alternative location.

14. The computer program product of claim 13, wherein the instructions further comprise:

determining an entry position of the endoscopic device into the cavity element and determining the navigation path from the determined entry position to the predetermined relative location;

modifying the determined entry position as a function of the technical embodiment of the sensor, as a function of the restricting condition that compromises the capacity for movement of the endoscopic device, or as a function of the technical embodiment of the sensor and the restricting condition;

or a combination thereof.

15. The computer program product of claim 11, wherein the instructions further comprise generating and outputting, by an output facility, a navigation instruction using the navigation signal.

16. The computer program product of claim 11, wherein the instructions further comprise:

determining a position of the sensor of the endoscopic device based on an image data record of the at least one digital image data record supplied by the imaging examination modality, based on a position signal supplied by a magnetic sensor, an optical locator, a mechanical/kinematic, kinematic, or robotic locator, or a combination thereof, or supplied by the endoscopic device, or a combination thereof;

transferring, outputting, or transferring and outputting the determined position to the digital model;

or a combination thereof.

17. The computer program product of claim 13, wherein the instructions further comprise automatically or semi-automatically controlling the endoscopic device along the navigation path, the controlling comprising automatically or semi-automatically controlling a control device connected to the endoscopic device using the navigation signal.

18. The computer program product of claim 11, wherein the registering takes place after receipt of the operating action.

19. The method of claim 1, wherein the technical embodiment of the sensor includes a symmetry of a tip of the endoscopic device, a geometry of the tip of the endoscopic device, a flexibility of the tip of the endoscopic device, a predetermined viewing angle of the sensor, an acquisition angle of the sensor, an angle of inclination, an angle of a surface of the sensor, or any combination thereof.

* * * * *